United States Patent [19]

Hamidi

[11] Patent Number: 4,897,080
[45] Date of Patent: Jan. 30, 1990

[54] FEED DEVICE FOR AN EPIDURAL NEEDLE

[76] Inventor: Lemar W. Hamidi, Thüringer Strasse 2, 5880 Lüdenscheid, German Democratic Rep.

[21] Appl. No.: 234,916

[22] Filed: Aug. 22, 1988

[30] Foreign Application Priority Data

Oct. 6, 1987 [DD] German Democratic Rep. .................................... 3733757

[51] Int. Cl.$^4$ ............................................. A61M 5/00
[52] U.S. Cl. ..................................... 604/117; 604/187
[58] Field of Search ................ 604/117, 118, 187, 198

[56] References Cited

U.S. PATENT DOCUMENTS 2,198,666  4/1940  Gruskin ................................ 604/117
4,424,058  1/1984  Parsons et al. ....................... 604/118
4,801,293  1/1989  Jackson ............................ 604/118 X Primary Examiner—Dalton L. Truluck
Attorney, Agent, or Firm—Edwin D. Schindler

[57] ABSTRACT

A feeding device for an epidural needle which includes a guide rail having a guide block with a needle holder being slidable thereon is disclosed. The invention further includes a piston having a piston rod which is positioned upon the guide block with the piston rod extending into a cylinder filled with a liquid. The piston, which is positioned on the piston rod, includes flow passages for a limited flow of liquid. The feeding device of the invention allows for a reliable recognition of the epidural space of a patient by maintaining a constant feeding speed for the needle, irrespective of the feeding pressure applied.

16 Claims, 1 Drawing Sheet

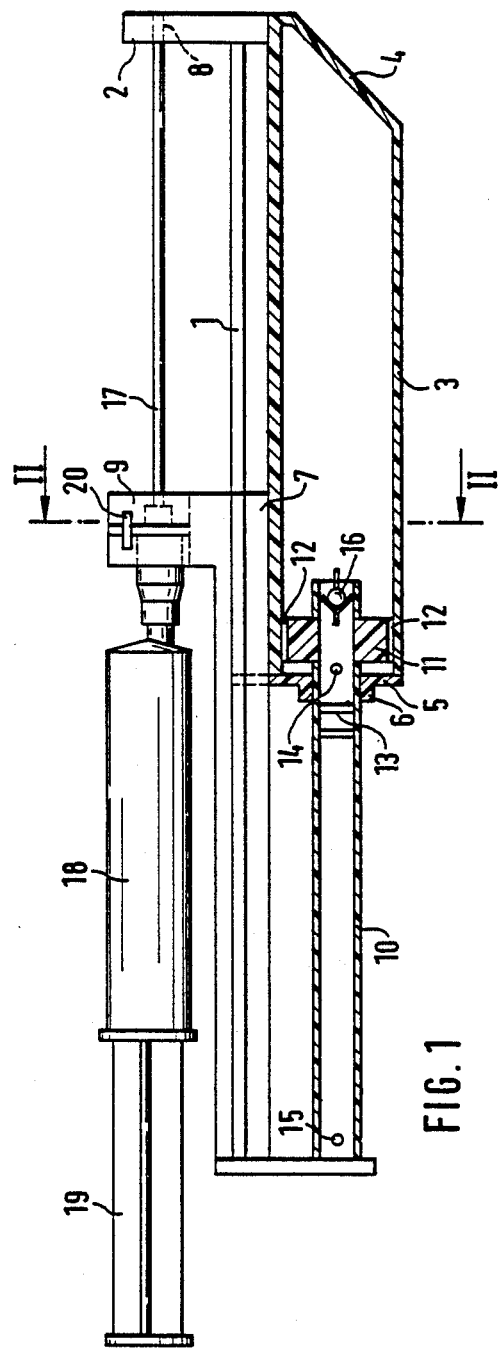
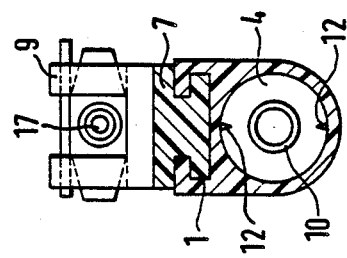

4,897,080

FEED DEVICE FOR AN EPIDURAL NEEDLE

BACKGROUND OF THE INVENTION

1. Field of the Invention

The invention relates to a feed device for the introduction of a needle into the epidural space.

2. Description of the Prior Art

In order to prepare the epidural anesthesia, a needle is introduced into the epidural space. The needle has a length of about 8 to 10 cm and is introduced through the back part. When traversing the ligamentum flavum, the feeding resistance is high. When the point of the needle penetrates into the epidural space, the resistance is reduced suddenly. Normally there is a slightly reduced pressure in the epidural space. This reduction in resistance and/or the low pressure is utilized as evidence for the penetration into the epidural space. The low pressure is determined according to the loss-of-resistance method or according to the hanging-drop method. However, these methods, nevertheless, are very risky, because there is the risk of a dura perforation, if the epidural space is not recognized, or the needle is moved forwards in an erratic manner after decrease of the resistance.

SUMMARY OF THE INVENTION

It is an object of the invention to provide a feed device, which allows for safe recognition of the epidural space and which keeps the feeding speed of the needle at a constant value irrespective of the feeding pressure.

The foregoing and related objects are accomplished by the feeding device of the present invention which includes a guide rail having a guide block with a needle holder being slidable thereon. The invention further includes a piston having a piston rod which is positioned upon the guide block with the piston rod extending into a cylinder filled with a liquid. The piston, which is positioned on the piston rod, includes flow passages for a limited flow of liquid.

The invention differs from the prior art in that the feeding speed is limited forcibly. The cylinder with the piston acts as a hydraulic brake so that irrespectively of the feeding pressure or the counterpressure of the tissue a given feeding speed cannot be exceeded. This remains true even after the decrease in feeding resistance occurs. Thus, the feed of the needle is effected slowly. Due to the fact that the feed device is further supported on the body of the patient, sudden feeding movements are excluded. Consequently the entering of the epidural space is reliably recognized. There is no risk that the needle might be advanced faster following the reduction of the counterpressure so as to perforate the dura; high viscosity is particularly preferred.

An immediate supporting on the back of the patient is reached in that the guide rail carries a supporting plate.

A secure guidance of the needle point is achieved in that, on the guide rail in the area of the supporting plate, a guide for the needle point is positioned.

A high hydraulic resistance is achieved in that the piston comprises, on the peripheral wall, one or more fine channels as flow passages.

A quick retracting of the guide block is rendered possible in that within the piston a back pressure valve is arranged, which closes in the direction of insertion of the needle.

Due to the fact that the liquid is incompressible, a compensation in volume, when inserting the piston rod into the cylinder, is rendered possible in that the piston rod is hollow, receives an interior piston and comprises, further to the piston, a passage for the liquid.

In order that the interior piston can be moved freely, it is provided that on the end, remote from the cylinder, of the piston rod, a ventilating passage is provided.

A secure recognition of the epidural space is possible in that the needle holder, receiving the needle, also receives a syringe with a piston rod, attachable on the needle. The syringe may be filled with water, saline solution or another physiologically compatible liquid. A pressure is exerted on the piston rod of the syringe, until the pressure decreases, when entering into the epidural space, and the content of the syringe is injected. Instead of this loss-of-pressure method it is also possible to utilize the hanging-drop method for the recognition of the epidural space.

BRIEF DESCRIPTION OF THE DRAWING

One embodiment of the invention will be described in the following with reference to the accompanying drawing, wherein FIG. 1 is a longitudinal section through he feed device, whilst FIG. 2 is a sectional along line II—II in FIG. 1.

DESCRIPTION OF THE PREFERRED EMBODIMENT

The feed device comprises a guide rail 1 with a supporting plate 2 on one end, which plate can be put on the back of the patient. The supporting plate 2 has a guide 8 for the needle. On the guide rail 1 a cylinder 3 is positioned, the front wall 4 of which being formed, adjacent to the supporting plate 2, in accordance with the anatomic details of the back, in order to guarantee a favorable placing and supporting on the back of the patient. The opposite front wall 5 of the cylinder 3 is provided as a plain plate with a passage 6. The cylinder 3 is filled with an incompressible hydraulic medium, particularly of high viscosity, designated as liquid in the following.

On the guide rail 1 a guide block 7 is slidably arranged. The guide block 7 carries a needle holder 9 for the reception of a usual needle 17, which is secured by a safety means 20 in its position. The guide block 7 is coupled, in addition, to a tubular piston rod 10, which extends through the passage 6 into the interior chamber of the cylinder 3. On the piston rod 10 a piston 11 is firmly positioned, which is slidably movable together with the piston rod 10 within the cylinder 3. In the peripheral surface of the piston 11 fine channels 12, extending substantially axially, are provided, which let pass just a limited amount of liquid when the piston rod 10 is displaced. The small cross-section of the channels 12 and the consequently high resistance to flow limit the movement of the piston rod 10 and, thus, of the guide block 7. The feed speed, therefore, is determined by the resistance to flow irrespective of the feeding pressure or the counterpressure of the tissue.

Within the hollow piston rod 10 an interior piston 13 is arranged freely displacably. In the end region of the piston rod 10 subsequent to the piston 11 and the chamber of the cylinder 3 a passage 14 for the liquid is positioned. At the end, remote therefrom, of the piston rod 10 a pressure release passage 15 is positioned. In addition, a back pressure valve 16 is provided, which blocks when the piston rod is displaced in the direction of insertion of the needle.

The needle holder 9 receives a needle 17, the point of which, or front end, being guided in the guide 8. On the needle 17 a syringe 18 with a piston rod 19 can be attached.

The function of the feed device will be described in the following. After preparation of the insertion field by sterilization and local anesthesia, the feed device is placed in the position according to FIG. 1 on the back of the patient. The feed device has a fixed position on the back of the patient. The guide block 7 is advanced by the anesthesiologist. In this connection the feed speed is determined by the reference to flow in the cylinder 3 so that the feeding speed does not exceed a given value. In the first part of the feeding movement, a mandrin or introducer is utilized in the usual manner; however that is not described herein. As soon as the point of the needle enters the epidural space through the ligamentum flavum, the feeding resistance decreases suddenly. However, an acceleration of the feeding movement is excluded so that the needle does not penetrate the dura through the epidural space. Consequently, the epidural space can be recognized reliably.

For this effect, the syringe 18 is filled with a saline solution, water, air or another physiologically compatible medium. A pressure is exerted to the piston rod. As long as the needle 17 penetrates tissue, the content of the syringe cannot escape. After the introduction of the needle 17 into the epidural space, the counterpressure disappears so that the content of the syringe can escape. In the case of this loss-of-pressure method, one pushes with the one hand to the feed device and with the other hand to the pressure piston.

Instead of this method, it is also possible to use the method of the hanging drop for the recognition of the peridural space.

Finally the anesthesia solution is introduced. That can be effected by the needle or by a catheter to be introduced especially; however, that is already known.

I claim the following:

1. A feeding device for the introduction of a needle, having a needle point, into the epidural space of a person, comprising:
   a guide rail;
   a needle;
   a needle holder for holding said needle;
   a guide block having said needle holder, said guide block being slidably arranged on said guide rail;
   a piston rod positioned on said guide block, said piston rod extending into a cylinder, through a passage, which is capable of being filled with a liquid; and,
   a piston positioned on said piston rod, said piston having a series of flow passages for a limited flow of the liquid.

2. The feeding device according to claim 1, further comprising a supporting plate carried upon said guide rail, said supporting plate being capable of placement upon the back of the person.

3. The feeding device according to claim 2, further comprising a guide for the needle point, said guide being located on said guide rail near said supporting plate.

4. The feeding device according to claim 1, further comprising a back pressure valve arranged in said piston, said back pressure valve being closeable in a direction of insertion of said needle.

5. The feeding device according to claim 1, wherein said piston rod is hollow, for reception of an interior piston, and further includes a passage for the liquid.

6. The feeding device according to claim 1, wherein a pressure release passage is provided at the end of said piston rod furthermost from said cylinder.

7. The feeding device according to claim 1, wherein said needle holder further receives a syringe with a second piston rod which is attachable to the needle.

8. A feeding device for the introduction of a needle, having a needle point, into the epidural space of a person, comprising:
   a guide rail;
   a needle;
   a needle holder for holding said needle;
   a guide block having said needle holder, said guide block being slidably arranged on said guide rail;
   a supporting plate carried upon said guide rail, said supporting plate being capable of placement upon the back of the person;
   a first piston rod positioned on said guide block, said first piston rod extending into a cylinder, through a passage, which is capable of being filled with a liquid;
   a piston positioned on said first piston rod, said piston having a series of flow passages for a limited flow of the liquid; and,
   a syringe having a second piston rod and being received by said needle holder.

9. The feeding device according to claim 8, further comprising a guide for the needle point, said guide being located on said guide rail near said supporting plate.

10. The feeding device according to claim 8, further comprising a back pressure valve arranged in said piston, said back pressure valve being closeable in a direction of insertion of said needle.

11. The feeding device according to claim 8, wherein said piston rod is hollow, for reception of an interior piston, and further includes a passage for the liquid.

12. The feeding device according to claim 8, wherein a pressure release passage is provided at the end of said piston rod furthermost from said cylinder.

13. A feeding device for the introduction of a needle, having a needle point, into the epidural space of a person, comprising:
   a guide rail;
   a needle;
   a needle holder for holding said needle;
   a guide block having said needle holder, said guide block being slidably arranged on said guide rail;
   a supporting plate carried upon said guide rail, said supporting plate being capable of placement upon the back of the person; a first piston rod positioned on said guide block, said first piston rod extending into a cylinder, through a passage, which is capable of being filled with a liquid;
   a piston positioned on said first piston rod, said piston having a series of flow passages for a limited flow of the liquid;
   a back pressure valve arranged in said piston, said back pressure valve being closeable in a direction of insertion of said needle; and,
   a syringe having a second piston rod and being received by said needle holder.

14. The feeding device according to claim 13, further comprising a guide for the needle point, said guide being located on said guide rail near said supporting plate.

15. The feeding device according to claim 13, wherein said piston rod is hollow, for reception of an interior piston, and further includes a passage for the liquid.

16. The feeding device according to claim 13, wherein a pressure release passage is provided at the end of said piston rod furthermost from said cylinder.

* * * * *

UNITED STATES PATENT AND TRADEMARK OFFICE
CERTIFICATE OF CORRECTION

PATENT NO.   : 4,897,080
DATED        : January 30, 1990
INVENTOR(S)  : Lemar W. Hamidi It is certified that error appears in the above-identified patent and that said Letters Patent is hereby corrected as shown below:

On the Cover Page, in the address of the Inventor, delete "German Democratic Republic" and substitute therefor --Federal Republic of Germany--.

Signed and Sealed this

Seventeenth Day of September, 1991

Attest:

HARRY F. MANBECK, JR.

*Attesting Officer*           *Commissioner of Patents and Trademarks*